United States Patent [19]

Shibamoto et al.

[11] Patent Number: 4,528,397

[45] Date of Patent: Jul. 9, 1985

[54] AMINOCARBOXYLIC ACID DERIVATIVES

[75] Inventors: Norio Shibamoto, Chigasaki; Takeo Yoshioka, Ayase; Yasuo Fukagawa, Kamakura; Tomoyuki Ishikura, Chigasaki, all of Japan

[73] Assignee: Sanraku-Ocean Co., Ltd., Tokyo, Japan

[21] Appl. No.: 479,982

[22] Filed: Mar. 29, 1983

[30] Foreign Application Priority Data

Mar. 30, 1982 [JP] Japan .................. 57-49950

[51] Int. Cl.³ .......................... C07C 101/24
[52] U.S. Cl. .................... 514/400; 562/439; 562/432; 562/503; 562/505; 562/506; 562/507; 562/400; 562/556; 562/560; 562/443; 562/564; 562/561; 562/441; 562/565; 562/448; 562/445; 562/426; 548/342; 548/561; 514/415; 514/562; 514/563; 514/564; 514/565
[58] Field of Search .............. 424/319, 309, 274, 273, 424/269; 562/426, 556, 560, 443, 564, 561, 441, 565, 448, 443, 439, 432, 503, 505, 506, 507, 400, 420; 548/342, 561; 424/319, 274, 273, 269

[56] References Cited

U.S. PATENT DOCUMENTS 2,452,653  11/1948  Harris et al. .................. 562/556
3,950,542  4/1976   Kalopissis et al. ............ 424/316
4,140,797  2/1979   Ondetti et al. ................ 424/319

FOREIGN PATENT DOCUMENTS 0010573  5/1980  European Pat. Off. ........... 424/319

OTHER PUBLICATIONS

Chemical Abstracts, vol. 60, No. 13, Jun. 1964, Abstract No. 15984c.
Chemical Abstracts, vol. 89, No. 22, Nov. 1978, Abstract No. 18659r.
Aleksier, Chem. Abst, vol. 88, #120743h (1978).

Primary Examiner—James H. Reamer
Attorney, Agent, or Firm—Wenderoth, Lind & Ponack

[57] ABSTRACT

An aminocarboxylic acid derivative represented by the formula

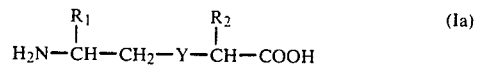

wherein $R_1$ and $R_2$, independently from each other, represent a hydrogen atom or an alkyl group which may have a substituent, and Y represents —NH— or —S—, provided that when Y represents —NH—, at least one of $R_1$ and $R_2$ represents an alkyl group which may have a substituent. These compounds have excellent inhibitory activity on dipeptidase in animals, and are useful for administration in combination with carbapenem antibiotics.

10 Claims, No Drawings

AMINOCARBOXYLIC ACID DERIVATIVES

This invention relates to a certain kind of aminocarboxylic acid derivatives and their use as a dipeptidase inhibitor. More specifically, this invention relates to novel compounds of the formula

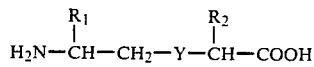

wherein $R_1$ and $R_2$, independently from each other, represents a hydrogen atom or an alkyl group which may have a substituent, and Y represents —NH— or —S— provided that when Y is —NH—, at least one of $R_1$ and $R_2$ represents an alkyl group which may be substituted;

and to the use of these compounds as a dipeptidase inhibitor.

In recent years, a group of carbapenem antibiotics having a basic skeletal structure of the following formula

have been discovered, and attracted attention as future antibiotics having a broad antimicrobial spectrum against Gram-negative, Gram-positive and β-lactamase-producing bacteria.

The mechanism by which these carbapenem antibiotics show antimicrobial activity is considered to be attributed to the inhibition of the cell walls of bacteria as is the case with β-lactam type antibiotics such as penicillin-type antibiotics and cephalosporin-type antibiotics. Accordingly, the carbapenem antibiotics have been desired to be developed rapidly as antimicrobial agents of selective toxicity which are useful for higher animals having no cell wall.

It is known, however, as reported, for example, in H. Kropp et al. Abstract No. 272, 20th Intersci. Conf. Antimicr. Agents & Chemoth., New Orleans, U.S.A. (1980) that the carbapenem antibiotics have the fatal defect of undergoing metabolism in vivo, particularly in the kidneys of animals and of being converted to inert substances. It is believed that this metabolization mechanism is the hydrolysis of their β-lactam ring by particle-bound dipeptidase present in the kidneys.

Some enzyme inhibitors have been discovered and proposed in order to inibit the metabolism of carbapenem antibiotics and increase the concentration and half-life period of these antibiotics in the blood by using them in combination with substances having dipeptidase inhibiting activity (see, for example, Japanese Laid-Open Patent Publication No. 51023/1980).

The present inventors previously discovered and proposed antibiotic PS-5 (Okamura et al., J. Antibiotics, Vol. 32, 262-271, 1979), and antibiotics PS-6 and PS-7 (Shibamoto et al., J. Antibiotics, Vol. 33, 1128-1137, 1980) as carbapenem antibiotics. The present inventors have also made extensive investigations about dipeptidase inhibitors for inhibiting the metabolism of these carbapenem antibiotics, and have now found that the aminocarboxylic acid compounds of formula (I) given above have strong dipeptidase inhibiting activity.

In the present specification, the term "lower" means that groups or compounds qualified by this term have not more than 6, preferably not more than 4, carbon atoms.

In formula (I), the alkyl group for $R_1$ and $R_2$ may be linear or branched. Generally, alkyl groups having not more than 10, especially not more than 6, carbon atoms are suitable. Examples include methyl, ethyl, n-propyl, isopropyl, n-butyl, isobutyl, sec-butyl, tert-butyl, n-pentyl, isopentyl, 1-methylbutyl, 1-ethylpropylneopentyl, tert-pentyl, n-hexyl, isohexyl, n-heptyl, n-octyl, n-nonyl, and n-decyl. These alkyl groups may have a substituent. Examples of the substituent on the alkyl group include cycloalkyl groups, especially lower cycloalkyl groups such as cyclopropyl, cyclobutyl, cyclopentyl and cyclohexyl; substituted or unsubstituted aryl groups such as phenyl, naphthyl and p-hydroxyphenyl; a hydroxyl group; a mercapto group; lower alkylmercapto groups such as methylmercapto; a carboxyl group; an amino group; a carbamoyl group; a guanidyl group; and 5- to 7-membered nitrogen-containing heterocyclic groups such as pyrrolidinyl, imidazolyl and indolyl. The alkyl group may be substituted by 1 to 3 such substituents.

Typical examples of the combination of $R_1$, $R_2$ and Y in the compounds of formula (I) used as a dipeptidase inhibitor are shown below.

$$\underset{H_2N-CH-CH_2-Y-CH-COOH}{\overset{R_1 \qquad\qquad R_2}{|\qquad\qquad\quad|}} \quad (I)$$

| $R_1$ | $R_2$ | Y |
|---|---|---|
| —H | —H | —NH— |
| —CH₃ | " | " |
| —CH(CH₃)₂ | " | " |
| —CH₂CH(CH₃)₂ | " | " |
| —CH₂CH(CH₃)CH₂CH₃ | " | " |
| —CH₂SH | " | " |
| —CH₂CH₂SCH₃ | " | " |
|  | " | " |
| 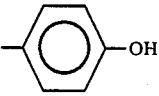 | " | " |
| 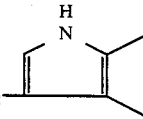 | " | " |
| —CH₂OH | " | " |
| —CH(OH)CH₃ | " | " |
| —CH₂—CONH₂ | " | " |
| —CH₂CH₂—CONH₂ | " | " |
| —CH₂COOH | " | " |
| —CH₂CH₂COOH | " | " |
| —CH₂(CH₂)₃NH₂ | " | " |
| 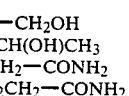 | " | " |

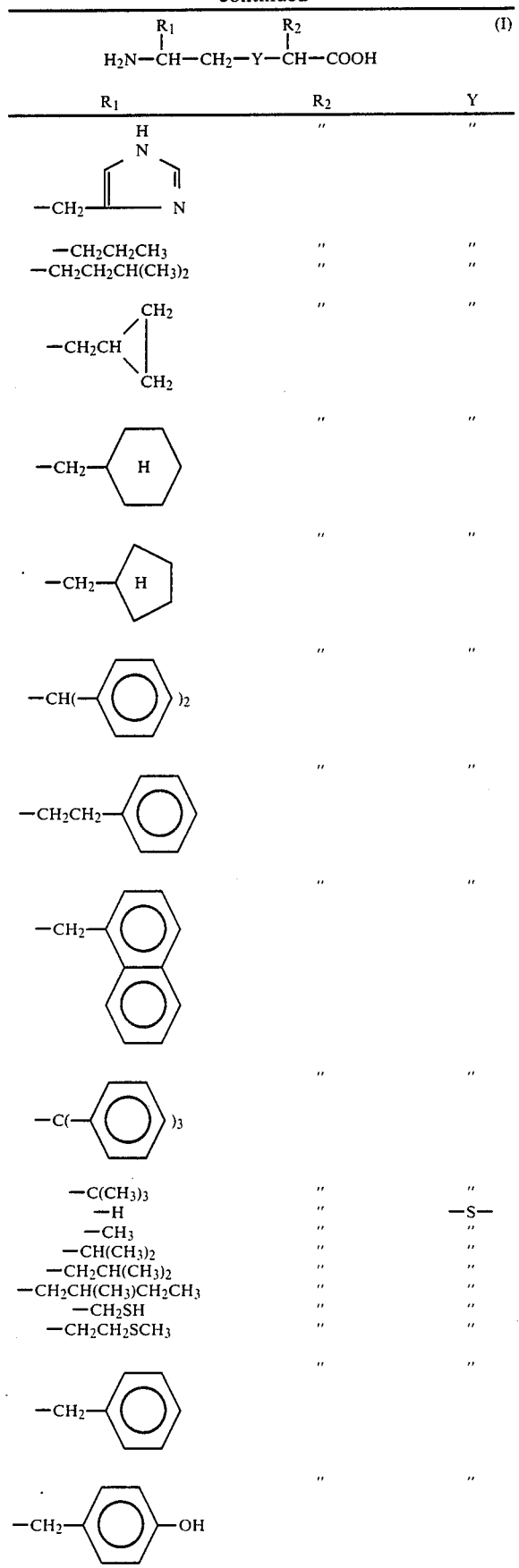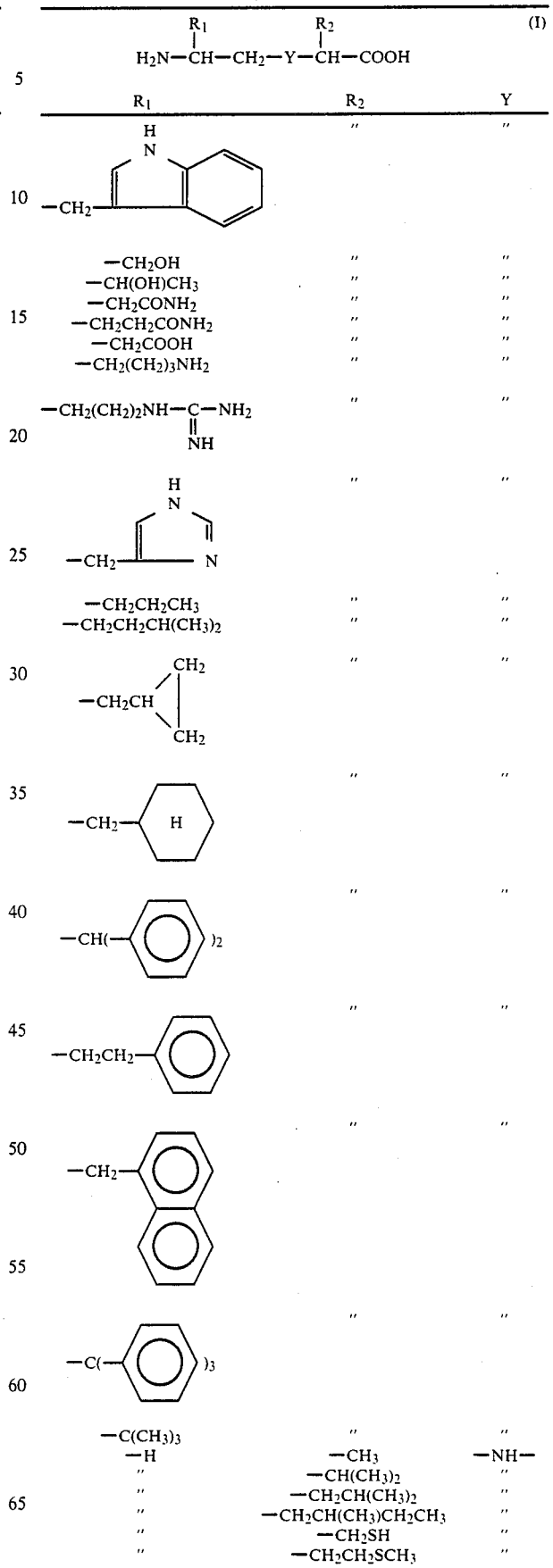

-continued $$H_2N-\underset{R_1}{\overset{}{C}H}-CH_2-Y-\underset{R_2}{\overset{}{C}H}-COOH \quad (I)$$

| R₁ | R₂ | Y |
|---|---|---|
| " | —CH₂—C₆H₅ | " |
| " | —CH₂—C₆H₄—OH | " |
| " | —CH₂-(indol-3-yl) | " |
| " | —CH₂OH | " |
| " | —CH(OH)CH₃ | " |
| " | —CH₂CONH₂ | " |
| " | —CH₂CH₂CONH₂ | " |
| " | —CH₂COOH | " |
| " | —CH₂CH₂COOH | " |
| " | —CH₂(CH₂)₃NH₂ | " |
| " | —CH₂(CH₂)₂N(H)—C(=NH)—NH₂ | " |
| " | —CH₂-(imidazol-4-yl) | " |
| " | —CH₂CH₂CH₃ | " |
| " | —CH₂CH₂CH(CH₃)₂ | " |
| " | —CH₂CH-(cyclopropyl) | " |
| " | —CH₂-(cyclohexyl) | " |
| " | —CH₂-(cyclopentyl) | " |
| " | —CH(C₆H₅)₂ | " |
| " | —CH₂CH₂—C₆H₅ | " |

-continued $$H_2N-\underset{R_1}{\overset{}{C}H}-CH_2-Y-\underset{R_2}{\overset{}{C}H}-COOH \quad (I)$$

| R₁ | R₂ | Y |
|---|---|---|
| " | —CH₂-(naphthyl) | " |
| " | —C(C₆H₅)₃ | " |
| " | —C(CH₃)₃ | " |
| " | —CH₃ | —S— |
| " | —CH(CH₃)₂ | " |
| " | —CH₂CH(CH₃)CH₂CH₃ | " |
| " | —CH₂SH | " |
| " | —CH₂CH₂SCH₃ | " |
| " | —CH₂—C₆H₅ | " |
| " | —CH₂—C₆H₄—OH | " |
| " | —CH₂-(indol-3-yl) | " |
| " | —CH₂OH | " |
| " | —CH(OH)CH₃ | " |
| " | —CH₂CONH₂ | " |
| " | —CH₂CH₂CONH₂ | " |
| " | —CH₂COOH | " |
| " | —CH₂CH₂COOH | " |
| " | —CH₂(CH₂)₃NH₂ | " |
| " | —CH₂(CH₂)₂NH—C(=NH)—NH₂ | " |
| " | —CH₂-(imidazol-4-yl) | " |
| " | —CH₂CH₂CH₃ | " |
| " | —CH₂CH₂CH(CH₃)₂ | " |
| " | —CH₂CH-(cyclopropyl) | " |
| " | —CH₂-(cyclohexyl) | " |

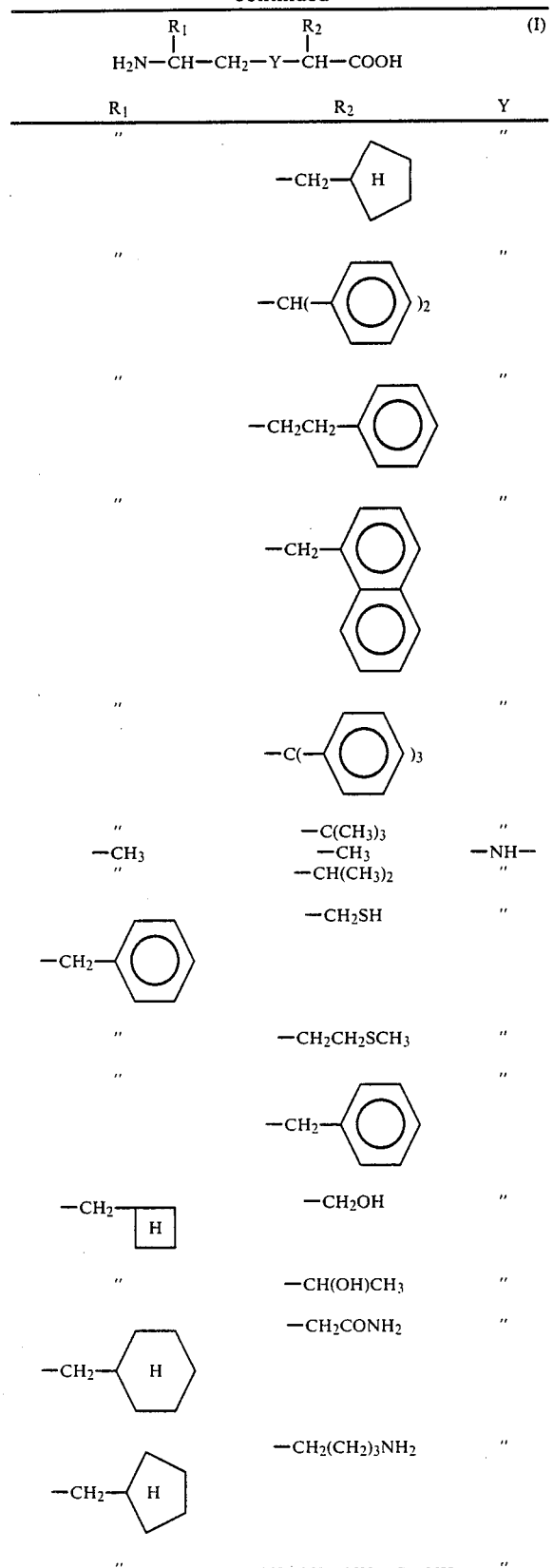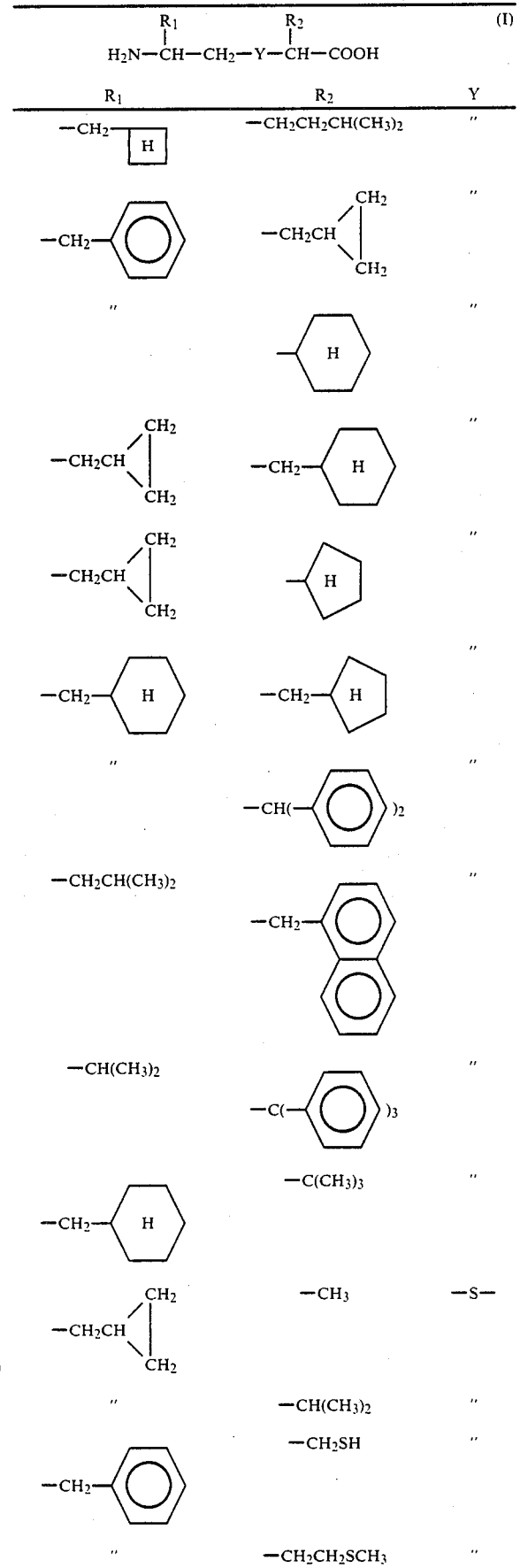

-continued $$\underset{(I)}{H_2N-\underset{R_1}{\overset{|}{C}H}-CH_2-Y-\underset{R_2}{\overset{|}{C}H}-COOH}$$

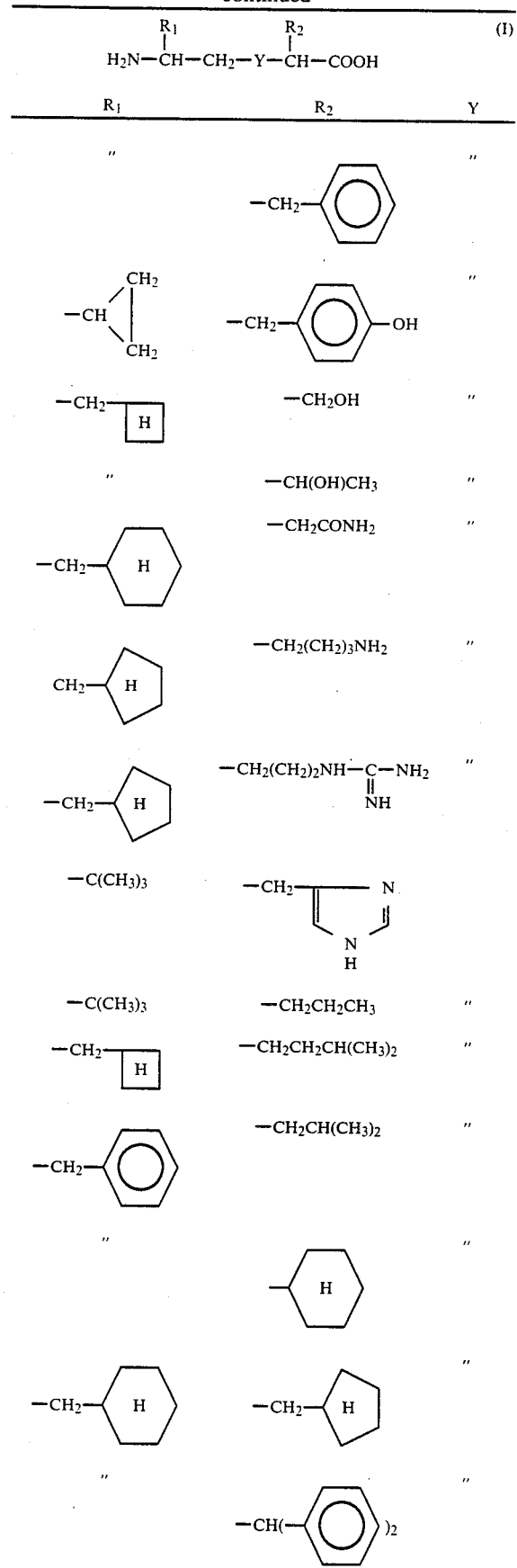

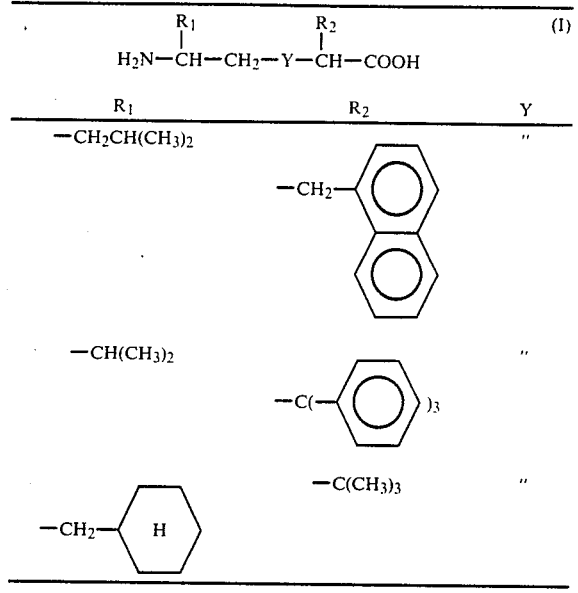

Compounds of formula (I) in which Y is —NH— are preferred as inhibitors in this invention. Especially preferred are those of formula (I) in which both $R_1$ and $R_2$ are hydrogen atoms, those of formula (I) in which $R_1$ is a lower alkyl group and $R_2$ is a hydrogen atom, and those of formula (I) in which $R_1$ represents a benzyl group and $R_2$ is a hydrogen atom.

Excepting compounds of formula (I) in which $R_1$ and $R_2$ are both hydrogen atoms and Y is —NH—, the compounds of formula (I) are novel compounds not described in the prior literature. The novel compounds of formula (I) can be synthesized in accordance with a method for producing the known compounds of formula (I), as schematically shown below.

Reaction scheme A

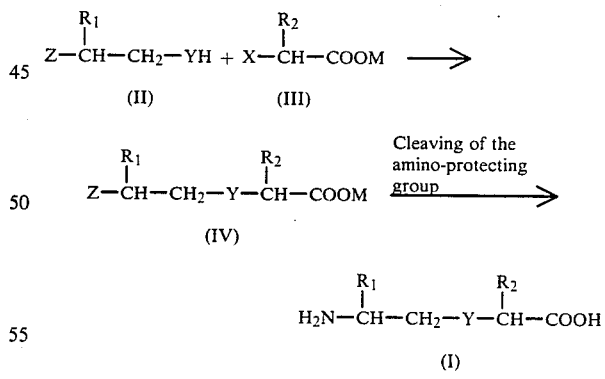

In the above scheme, Z represents an amino group or a protected amino group (e.g., a tert-butoxy-carbonylamino group, a phthaloylimide group, an acetylamino group, a benzylamino group, a p-methoxybenzylamino group, etc.); X represents a halogen atom, or further, X represents a hydroxyl group when Y is —NH—; M represents a hydrogen atom or a cation; and $R_1$, $R_2$ and Y are as defined hereinabove.

Reaction Scheme B

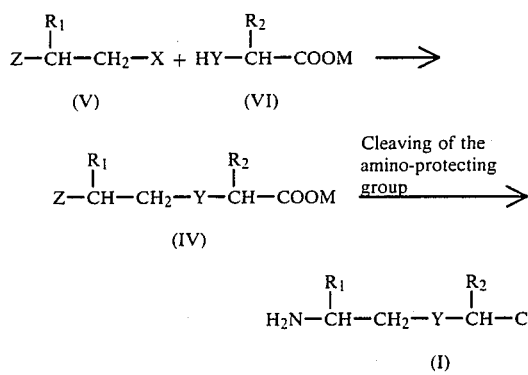

In the above scheme, $R_1$, $R_2$, Y, Z, X and M are as defined hereinabove.

The reaction between the compound of formula (II) and the compound of formula (III) in reaction scheme A, or the reaction between the compound of formula (V) and the compound of formula (VI) in reaction scheme B can be carried out usually in a suitable solvent such as water, N,N-dimethylformamide, tetrahydrofuran, methanol, ethanol and methylene chloride at a temperature of about 0° C. to the refluxing temperature of the reaction mixture.

When X represents a halogen atom in the reaction schemes A and B, the reaction between the compound of formula (II) and the compound of formula (III), and the reaction between the compound of formula (V) and the compound of formula (VI) are desirably carried out in the presence of a base such as triethylamine or pyridine.

On the other hand, when X represents a hydroxyl group and Y represents —NH— in the reaction schemes A and B, the compound of formula (IV) can be obtained by first oxidizing the compound of formula (III) or the compound of formula (V), reacting the oxidation product (aldehyde) with the compound of formula (II) or the compound of formula (VI), and thereafter reducing the reaction product (Schiff base) with a conventional reducing agent.

The ratio of the compound (III) to the compound (II) or the ratio of the compound (VI) to the compound (V) is not critical. Generally, it is proper to use the compound of formula (III) or (VI) in a proportion of 1.0 to 3.0 moles per mole of the compound of formula (II) or the compound of formula (V).

Cleaving of the amino-protecting group in the resulting compound of formula (IV) can be carried out by methods known per se, for example by hydrolysis or hydrogenolysis.

The details of the methods for producing the compounds of formula (I) shown in reaction schemes A and B above will be shown in Examples to be given hereinafter.

As stated above, the compounds of formula (I) have the activity of effectively inhibiting the enzymatic activity of dipeptidase present in the body of mammals, especially in their kidneys, and are useful ad dipeptidase inhibitors. The excellent dipeptidase inhibiting activity of the compounds of formula (I) is provided by the following in vitro experiments.

(1) Purification of dipeptidase

Rats were sacrificed by decapitation, and about 12 g of fresh kidneys were collected. A microsome fraction was obtained by the Hogboom's subcellular fractionating method used on differential centrifugation (Methods in Enzymology, Vol. 1, pages 16-19, Academic Press, New York, 1955). The microsome fraction was treated with 400 μg/ml of trypsin at 0° C. for 16 hours, and then supercentrifugally fractionated at $10^5$ G for 60 minutes at 0° C.

The resulting precipitate was suspended in 20 ml of tris-HCl buffer (20 mM, pH 7.6) containing a detergent (0.4% Triton X-100), and then supercentrifugally fractionated at $10^5$ G for 60 minutes at 0° C. The supernatant liquid was charged onto a column (15×100 mm) of Sephadex A-50 (Cl-form), and the column was eluted with tris-HCl buffer (20 mM, pH 7.0) containing a detergent (0.4% Triton X-100) with a sodium chloride concentration linear gradient from 0 to 0.5M.

The active fractions were concentrated with polyethylene glycol 4000, and then successively purified by a Sephadex G-150 (25×900 mm) column and a Sephadex G-200 (25×900 mm) column using the same tris-HCl buffer as above to obtain a partially purified sample of the dipeptidase.

(2) Measurement of inhibitory activity

Fifty microliters of the enzyme obtained as above was preincubated together with 30 μl of an inhibitor solution in a cuvette at 37° C. for 5 minutes. Then, 2.82 ml of a solution of glycyldehydrophenylalanine ($5.3\times10^{-5}$M) preincubated to 37° C. as a substrate in tris-HCl (0.1M, pH 8.0) was added, and the reaction was started. The reaction was carried out in a cuvette of a Hitachi spectrophotometer equipped with a constant temperature (37° C.) device, and by a recorder, a decrease in the absorbance of the reaction mixture at a wavelength of 275 nm during 5 minutes was measured.

The same experiment as above was carried out using a tris-HCl (pH 8.0) solution of antibiotic PS-5 (1.03 mM) as a substrate, and a decrease in the absorbance of the reaction mixture at a wavelength of 300 nm during 5 minutes was measured.

The percent inhibition and $ID_{50}$ at a predetermined inhibitor concentration were determined from the measured values obtained as above and that obtained in a control in which no inhibitor was used.

The results are summarized in Table 1.

TABLE 1

Compound: $NH_2-\overset{R_1}{\underset{|}{CH}}-CH_2-Y-\overset{R_2}{\underset{|}{CH}}-COOH$

| Dipeptidase inhibitor | $R_1$ | Y | $R_2$ | Inhibition at $10^{-4}$M (%) | $ID_{50}$ |
|---|---|---|---|---|---|
| 1 | H | NH | H | 86 | $1.0\times10^{-4}$M |
| 2 | H | S | H | 2 | |
| 3 | H | NH | $CH_3-$ | 15.6 | |

TABLE 1-continued

Compound: $NH_2-\underset{R_1}{CH}-CH_2-Y-\underset{R_2}{CH}-COOH$

| Dipeptidase inhibitor | $R_1$ | Y | $R_2$ | Inhibition at $10^{-4}M$ (%) | $ID_{50}$ |
|---|---|---|---|---|---|
| 4 | H | NH | -CH$_2$-C$_6$H$_5$ | 38.0 | |
| 5 | C$_6$H$_5$-CH$_2$- | NH | H | 85 | $0.22 \times 10^{-4}M$ |
| 6 | CH$_3$- | NH | H | 42.4 | |

As stated hereinabove, the compounds of formula (I) have excellent inhibitory activity on dipeptidase in animals, and are considered to be useful for administration in combination with carbapenem antibiotics in order to inhibit the in vivo metabolism of the carbapenem antibiotics, particularly their metabolism in kidneys.

The synergistic effect by this coadministration is proved by the following in vivo test.

Coadministration of N-(2-aminoethyl)glycine and antibiiotic PS-5

To groups of 5 mice each (male, ddY, aged 5 weeks) was orally administered 0.25 ml (20 mg/mouse) of an aqueous solution of N-(2-aminoethyl)glycine (AEG) in a concentration of 80 mg/ml (the solutions had been adjusted to pH 7.5 with 1N HCl). The same volume of pure water was administered to a control group. Thirty minutes later, 0.25 ml of a solution of antibiotic PS-5 Na salt (8 mg/ml) in M/100 PBS (pH 7.0) was subcutaneously administered. Blood was taken from the retroorbital sinus at various time intervals using a heparinized capillary (a thermohematocrit capiratry tube, total length 75 mm, outside diameter 1.45–1.65 mm). One end of the tube was sealed with IATROSEAL® (Iatron Laboratries) and the plasma was separated by centrifugal separation (3000 rpm, 10 minutes). Blood sampling was carried out a total of six times at 0 time (immediately before administration of the antibiotic PS-5) and 5 minutes, 15 minutes, 30 minutes, 60 minutes and 90 minutes after the administration of the antibiotic PS-5. The concentration of the antibiotic PS-5 in the plasma was disc-assayed against *Comamonas terrigena* B-996. From the measured values, the average value for five mice±standard error was calculated, and is shown in Table 2.

On the other hand, the whole urine of the mice was taken 3 hours after the administration of the antibiotic PS-5, and the concentration of the antibiotic PS-5 in the collected whole urine was assayed by the same method as above. The mean concentrations for five mice was calculated. The results are also shown in Table 2.

TABLE 2

| | Concentration of antibiotic PS-5 in the plasma (μg/ml) | |
|---|---|---|
| Time (min.) | AEG administered group | Control group |
| 0 | 0 | 0 |
| 5 | 49.6 ± 3.7 | 52.0 ± 4.6 |
| 15 | 21.7 ± 2.6 | 15.2 ± 1.9 |
| 30 | 2.3 ± 0.5 | 1.0 ± 0.1 |
| 60 | 0 | 0 |
| 90 | 0 | 0 |
| Urinary recovery (0–3 hrs.) | 13.2% | 0 |

Examples of the cabapenem antibiotics which prove to be effective when combined with the compounds of formula (I) are antibiotics PS-5, PS-6 and PS-7, thienamycin, formimidoyl thienamycin, epithienamycin, carpetimycin, asparenomycin, olivanic acid, SF2103A and derivatives of these. Advantageously, the carbapenem antibiotic is combined in an amount of generally 1/20 to 20 parts by weight, especially 1 to 5 parts by weight, per part by weight of the compound of formula (I).

The compound of formula (I) in accordance with this invention can be administered orally or parenterally (e.g., intramuscularly, intravenously, or intrarectally) in the form of a mixture with such a carbapenem antibiotic, or a formulation different from the carbapenem antibiotic. The dosage of the compound of formula (I) is usually 0.1 to 5 g/kg/day, preferably 100 to 1000 mg/kg/day. On the other hand, the carbapenem antibiotic can be administered in usual dosages, for example 100 to 5000 mg/kg/day, preferably 100 to 1000 mg/kg/day. By this, infectious diseases of man and other animals can be prevented, treated or medicated.

In administering the compound of formula (I) and the carbapenem antibiotic orally or parenterally, they can be formulated into a solid form such as tablets, capsules, sugar-coated pills or suppositories, or a liquid form such as a solution, suspension or emulsion either separately or together as a mixture. These formulations may be prepared in a customary manner (galenical preparation) using ordinary pharmaceutically acceptable solid or liquid inert carriers or diluents suitable for oral or parenteral administration, for example water, gelatin, lactose, starch, magnesium stearate, talc, vegetable oils, gum arabic, polyalkylene glycols and yellow vaseline.

The following Examples specifically illustrate the production of the compounds of formula (I).

EXAMPLE 1

Production of N-(2-aminoethyl)glycine

Bromoacetic acid (25 g; 0.18 mole) was dissolved in 100 ml of water, and at room temperature, 100 ml of water containing 10.8 g (0.36 mole) of ethylenediamine was added. They were reacted at 100° C. for 4 hours. The reaction solution was diluted to 3 liters with water and adsorbed on a column of 1 liter of Diaion PA306S (OH form). The column was washed with water and then eluted with 0.5N HCl. Eluate fractions which showed color reaction with ninhydrin at an Rm value of 1.7 (the mobility of alanine was taken as 1.0) in high-voltage paper electrophoresis (pH 1.8; 85% formic acid:acetic acid:water=25:75:900) were collected and dried under reduced pressure. The residue was dissolved in water and adsorbed onto a column of 500 ml of Dowex 50W (H form). The column was washed with water, and then eluted with 3N hydrochloric acid. Those eluate fractions which showed color reaction with ninhydrin were collected, and dried under reduced pressure. Crystallization of the residue from water-ethanol afforded 9.6 g of the dihydrochloride of the captioned compound as colorless needles.

Melting point: 165°-168° C.

Elemental analysis (for $C_4H_{12}N_2O_2Cl_2 \cdot \frac{1}{2}H_2O$): Found (%) C: 24.18%, H: 6.33, N: 14.03. Calcd. (%) C: 24.01, H: 6.55, N: 14.00.

IR Spectrum (KBr): 3430, 3200-2400 cm$^{-1}$ ($NH_2$, $NH_3^+$, $NH^+$), 1725 cm$^{-1}$ (COOH).

NMR Spectrum ($D_2O$; internal standard DSS): $\delta 3.30$-3.65 (4H, m, —$CH_2$—$CH_2$—), 4.01 (2H, S, N—$CH_2$—COO).

EXAMPLE 2

Production of N-(2-aminoethyl)-L-phenylalanine

L-phenylalanine (1.69 g; 10 mmoles) was dissolved in 10 ml of 1N sodium hydroxide, and then 20 ml of a dioxane solution containing 2.54 g (10 mmoles) of phthaloyl ethyl bromide was added. They were reacted at 100° C. for 5 hours. The reaction solution was allowed to cool, and 20 ml of 1N sodium hydroxide was added. The mixture was stirred at room temperature for 18 hours, and adjusted to pH 2.0 with 6N HCl. Then, 200 ml of 2N HCl was added, and the solution was hydrolyzed at 100° C. for 8 hours. The reaction solution was dried under reduced pressure, and then dissolved in 200 ml of water. The solution was adsorbed to a column of 300 ml of Amberlite CG 50 (H form) at a pH of 6.5. The column was washed with water, and then eluted with 0.2N HCl. Eluate fractions which showed color reaction with ninhydrin at an Rm value of 1.1 in high-voltage paper electrophoresis (pH 1.8; 85% formic acid:acetic acid:water=25:75:900) were collected and dried under reduced pressure. The residue was adsorbed on a column of Diaion PA306S (OH form) at a pH of 3.5. The column was washed with water and then eluted with 1N HCl. Eluate fractions which showed color reaction with ninhydrin were collected, and dried under reduced pressure. Crystallization of the residue from water-ethanol afforded 316 mg of the monohydrochloride of the captioned compound as colorless needles.

Melting point: 233°-234° C. (decomp.)

$[\alpha]_D^{24}$: 3.6° (C=1.0, $H_2O$)

Elemental analysis (for $C_{11}H_{17}N_2O_2Cl$): Found (%) C: 53.53, H: 6.94, N: 11.95, Cl: 14.59. Calcd. (%) C: 53.99, H: 7.00, N: 11.45, Cl: 14.49.

IR Spectrum (KBr): 3300-2000 cm$^{-1}$ ($NH_3^+$, $NH_2^+$), 1595 cm$^{-1}$ (COO—).

NMR Spectrum ($D_2O$+DCl; internal standard DSS): $\delta 3.15$-3.50 (6H, m, N—$CH_2$—$CH_2$—N, CH—$CH_2$—), 4.30 (1H, t, J=6.0 Hz, C$\underline{H}$—$CH_2$—), 7.33 (5H, s, phenyl group).

EXAMPLE 3

Production of N-(2-aminoethyl)-L-alanine

L-alanine (930 mg; 10 mmoles) was reacted and treated in the same way as in Example 2. There was obtained 217 mg of the monohydrochloride of the captioned compound as colorless needles which showed color reaction with ninhydrin at an Rm value of 1.3 in high-voltage paper electrophoresis (pH 1.8).

Melting point: 258° C. (decomp.)

$[\alpha]_D^{24}$: −2.4° (C=1.0, $H_2O$)

Elemental analysis (for $C_5H_{13}N_2O_3Cl$): Found (%) C: 35.40, H: 7.72, N: 16.06, Cl: 20.91. Calcd. (%) C: 35.61, H: 7.77, N: 16.61, Cl: 21.03.

IR Spectrum (KBr): 3200-2400 cm$^{-1}$ ($NH_3^+$, $NH_2^+$), 1645 cm$^{-1}$ (COO—).

NMR Spectrum ($D_2O$+DCl; internal standard DSS): $\delta 1.60$ (3H, d, J=7.5 Hz, $CH_3$—CH), 3.43 (4H, s, N—$CH_2$—$CH_2$—N), 4.12 (1H, q, J=7.5 Hz, C$\underline{H}$—$CH_3$).

EXAMPLE 4

Production of (S)-N-(2-aminopropyl)glycine (4-1) Synthesis of (S)-(1-hydroxymethyl)ethyl phthalimide L-alanine methyl ester hydrochloride (15.7 g) was dissolved in 100 ml of water, and under ice cooling, 10 g of sodium borohydride was gradually added. They were reacted at room temperature for 18 hours. The excess of the reagent was decomposed with acetic acid, and the residue was adsorbed on a column of 500 ml of Amberlite CG-50 (H form) at a pH of 6.0. When eluate fractions which showed color reaction with ninhydrin were dried, 8.5 g of (S)-2-amino-1-propanol was obtained. This product was dissolved in 200 ml of water containing 8.06 g (0.076 mole) of sodium carbonate, and then 16.7 g (0.076 mole) of N-carboethoxyphthalimide dissolved in 500 ml of methylene chloride was added. The mixture was vigorously stirred at room temperature for 16 hours. The reaction solution was adjusted to pH 2.0, and extracted with chloroform. The extract was dried, and the residue was dissolved in benzene. The solution was adsorbed on a column of 800 ml of silica gel. The column was eluted with benzene, a benzene/ethyl acetate mixed solvent (10:1), and a benzene/ethyl acetate mixed solvent (4:1) in this order. Eluate fractions which had an ultraviolet absorption at an Rf value of 0.32 in silica gel thin-layer chromatography developed with a benzene/ethyl acetate mixed solvent (2:1) were dried under reduced pressure to give 10.8 g of the captioned compound.

$[\alpha]_D^{24}$: 10.1° (C=1.0, $CHCl_3$).

IR Spectrum ($CHCl_3$): 1770, 1705 cm$^{-1}$ (phthaloyl CO).

NMR Spectrum ($CHCl_3$): $\delta 1.47$ (3H, d, J=7.0 Hz, $CH_3$—CH), 3.10 (1H, m, OH), 3.70-4.25 (2H, m, CH—CH$_2$—OH), 4.30–4.72 (1H, M, —CH—CH$_2$), 7.60–7.88 (4H, m, phthaloyl group).

(4-2) Synthesis of (S)-(1-p-toluenesulfonyloxymethyl)ethyl phthalimide (S)-(1-hydroxymethyl)ethylphthalimide (6.15 g; 0.03 mole) was dissolved in 80 ml of methylene chloride and 50 ml of pyridine, and under ice cooling, 11.4 g (0.06 mole) of tosyl chloride was added. They were reacted at room temperature for 16 hours. Chloroform and water were added to the reaction solution. The chloroform layer was washed with water and then with 2N HCl. The extract was concentrated under reduced pressure. The residue was dissolved in benzene, and adsorbed on a column of 500 ml of silica gel. The column was eluted with a benzene/ethyl acetate mixed solvent (20:1) and a benzene/ethyl acetate mixed solvent (10:1) in this order. Eluate fractions which had an ultraviolet absorption at an Rf value of 0.71 in silica gel thin-layer chromatography developed with a benzene/ethyl acetate mixed solvent (2:1) were collected, and dried under reduced pressure to give 8.47 g of the captioned compound.

$[\alpha]_D^{24}$: 20.0° (C=1.0, CHCl$_3$)

IR Spectrum (CHCl$_3$): 1780, 1715 cm$^{-1}$ (phthaloyl CO) 1395, 1370, 1180 cm$^{-1}$ (OSO$_2$R).

NMR Spectrum (CDCl$_3$): δ1.40 (3H, d, J=7.0 Hz, CH$_3$—CH), 2.33 (3H, s,

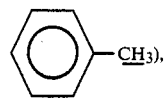

4.00–4.70 (3H, m, CH$_3$—CH—CH$_2$—O), 7.08 (2H, d, J=9.0 Hz, Ar.H), 7.57 (2H, d, J=9.0 Hz, Ar.H), 7.64 (4H, s, phthaloyl group).

(4-3) Synthesis of (S)-(1-azidomethyl)ethyl phthalimide

Sodium azide (4.9 g; 0.075 mole) was added to a methylene chloride solution of 12.4 g (0.075 mole) of tetraethyl ammonium chloride, and they were reacted at room temperature for 3 hours. The reaction mixture was filtered, and the filtrate was dried under reduced pressure. The residue was dissolved in 150 ml of anhydrous acetone, and 5.4 g (0.015 mole) of (S)-(1-p-toluenesulfonyloxymethyl)ethyl phthalimide was added. The mixture was refluxed for 18 hours. The reaction solution was concentrated under reduced pressure. The residue was dissolved in chloroform, and the chloroform layer was washed twice with water. The solvent was evaporated, and the residue was dissolved in a small amount of benzene. The solution was adsorbed on a column of 300 ml of silica gel, and the column was eluated with a benzene/ethyl acetate mixed solvent (20:1). Eluate fractions which showed an ultraviolet absorption at an Rf value of 0.79 in silica gel thin-layer chromatography developed with a benzene/ethyl acetate mixed solvent (4:1) were collected and concentrated to give 2.57 g of the captioned compound. Furthermore, by using the same mixed solvent (10:1), 1.24 g of the starting material was recovered.

$[\alpha]_D^{24}$: 48.5° (C=1.0, CHCl$_3$).

IR Spectrum (CHCl$_3$): 2190 cm$^{-1}$ (N$_3$), 1765, 1705 cm$^{-1}$ (phthaloyl CO).

NMR Spectrum (CDCl$_3$): δ1.47 (3H, d, J=7.5 Hz, CH$_3$—CH), 3.40–4.25 (2H, m, CH—CH$_2$—N$_3$), 4.30–4.70 (1H, m, CH$_3$—CH—CH$_2$), 7.60–7.85 (4H, m, phthaloyl group).

(4-4) Synthesis of (S)-(1-aminomethyl)ethylphthalimide

Five hundred milligrams of (S)-(1-azidomethyl)ethylphthalimide was dissolved in 30 ml of ethanol and 5 ml of 1N HCl, and then 200 mg of 10% Pd-C was added. It was catalytically reduced at room temperature and 4.5 atmospheres for 3 hours. The reaction product was filtered, and the filtrate was dried under reduced pressure. Ethyl acetate was added, and the precipitate was collected by filtration to give 361 mg of the hydrochloride of the captioned compound. This product showed color reaction with ninhydrin at an Rf value of 0.29 in silica gel thin-layer chromatography developed with methanol.

$[\alpha]_D^{24}$: 28.7° (C=1.0, methanol)

IR Spectrum (KBr): 3150–2500 cm$^{-1}$ (NH$_3$$^+$) 1780, 1700 cm$^{-1}$ (phthaloyl CO).

NMR Spectrum (DMSO-d$_6$+D$_2$O): δ1.45 (3H, d, J=7.5 Hz, CH$_3$—CH), 3.13 (1H, dd, J=14.0 Hz, J=4.0 Hz, CH—CHH—), 3.49 (1H, dd, J=14.0 Hz, J=11.0 Hz, CH—CHH—), 4.50 (1H, m, CH—CH$_2$—), 7.83 (4H, s, phthaloyl group).

(4-5) Production of (S)-N-(2-aminopropyl)glycine 1.5 g (6.23 mmoles) of (S)-(1-aminoethyl)ethylphthalimide hydrochloride was dissolved 60 ml of 50% methanol-water, and 900 mg of sodium borohydride was added at room temperature. They were reacted at room temperature for 1 hour. The reaction solution was adjusted to pH 6.5 and adsorbed on a column of Amberlite CG-50 (H form). The column was washed with water, and the resin was transferred into a beaker. A fraction eluted with 2N ammonium hydroxide was dried under reduced pressure. The residue (1.13 g) was a single substance which showed color reaction with ninhydrin at an Rf value of 0.16 in silica gel thin-layer chromatography developed with methanol. This showed the conversion to (S)-(2-o-hydroxymethylbenzoylamino)propylamine. The residue was dissolved in 6 ml of dioxane and 20 ml of water, and 6.82 mg (5.94 mmoles) of sodium glyoxylate was added. The mixture was stirred at room temperature for 1 hour. Furthermore, 1 g of sodium borohydride was added and reacted at the same temperature for 2 hours. The reaction mixture was passed through a column of 200 ml of Amberlite CG-50 (H form) at a pH of 5.0. The fractions were dried under reduced pressure, and then 120 ml of concentrated hydrochloric acid was added. The mixture was subjected to hydrolysis at 40° C. for 18 hours. The product was dried under reduced pressure. The residue was dissolved in water (pH 3.0) and adsorbed on a column of 200 ml of Dowex 50W (H form). The column was washed with water, and eluted with 3N ammonium hydroxide. A substance which showed color reaction with ninhydrin at an Rm value of 1.30 in high-voltage paper electrophoresis at a pH of 1.8 was obtained as an eluate. This fraction was dried under reduced pressure, and further adsorbed on a column of Diaion PA-306S (OH form). The column was washed with water, and then with 1N HCl. Fractions which showed color reaction with ninhydrin were dried under reduced pressure, and crystallized from ethanol to give 297 mg of the dihydrochloride of the captioned compound. This compound was dissolved in water, and adjusted to pH 4.0 with Diaion PA-306S (OH form). It was precipitated with methanol-ethanol, and the precipitate was collected by filtration to give the monohydrochloride of the captioned compound. These powders were hydroscopic.

NMR Spectrum (D$_2$O+DCl): δ1.46 (3H, d, J=7.0 Hz, CH$_3$), 3.09-4.13 (3H, m, CH—CH$_2$), 4.03 (2H, s, NH—CH$_2$—COOH).

Dihydrochloride $[\alpha]_D^{24}$: 2.2° (C=1.0, H$_2$O)

IR Spectrum (KBr): 3100-2500 cm$^{-1}$ (NH$_3^+$, NH$_2^+$) 1745 cm$^{-1}$ (COOH).

Elemental analysis (for C$_5$H$_{14}$N$_2$O$_2$Cl$_2$):

Found (%) C: 29.74, H: 6.97, N: 13.90. Calcd. (%) C: 29.28, H: 6.88, N: 13.66.

Monohydrochloride $[\alpha]_D^{24}$: 5.0° (C=1.0, H$_2$O)

IR Spectrum (KBr): 3100-2500 cm$^{-1}$ (NH$_3^+$, NH$_2^+$) 1630 cm$^{-1}$ (COO$^-$).

EXAMPLE 5

Production of (S)-[N-(2-amino-2-benzyl)ethyl]glycine (5-1) Synthesis of (S)-(1-benzyl-2-hydroxy)ethylphthalimide 1.18 g of (2-amino-3-phenyl)-1-propanol and 669 mg (6.39 mmoles) of sodium carbonate were dissolved in 30 ml of water, and 50 ml of methylene chloride containing 1.38 g (6.39 mmoles) of N-carboethoxyphthalimide was added. They were reacted for 18 hours. The reaction mixture was extracted in the same way as in (4-1) of Example 4. The extract was adsorbed on a column of 120 ml of silica gel, and the column was eluted with a benzene/ethyl acetate mixed solvent (5:1). An eluate fraction which showed an ultraviolet absorption at an Rf value of 0.55 in silica gel thin-layer chromatography developed with a benzene/ethyl acetate mixed solvent (1:1) was dried under reduced pressure to give 1.84 g of the captioned compound.

$[\alpha]_D^{24}$: −132.8° (C=1.0, CHCl$_3$).

IR Spectrum (CHCl$_3$): 1770, 1705 cm$^{-1}$ (phthaloyl CO).

NMR Spectrum (CDCl$_3$): δ2.80 (1H, m, OH), 3.20 (2H, d, J=7.5 Hz,

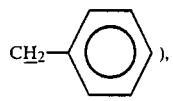), 3.75-4.25 (2H, m, —CH$_2$—O), 4.60 (1H, m, CH$_2$—CH—CH$_2$), 7.30 (5H, s, phenyl group), 7.50-7.80 (4H, m, phthaloyl group).

(5-2) Synthesis of (S)-(1-benzyl-2-p-toluenesulfonyloxy)ethyl phthalimide 2.81 g (0.01 mole) of (S)-(1-benzyl-2-hydroxy)ethyl phthalimide was dissolved in 30 ml of pyridine and 20 ml of methylene chloride. Under ice cooling, 50 ml of a methylene chloride solution containing 3.8 g (0.02 mole) of tosyl chloride was added. They were reacted at room temperature for 18 hours. The reaction mixture was worked up in the same way as in (4-2) of Example 4, and charged onto a column of 300 ml of silica gel. The column was eluted with a benzene/ethyl acetate mixed solvent (10:1). Eluate fractions which had an ultraviolet absorption at an Rf value of 0.72 in silica gel thin-layer chromatography developed with a benzene/ethyl acetate mixed solvent (4:1) were collected and dried under reduced pressure to give 3.48 g of the captioned compound. $[\alpha]_D^{24}$: −59.6° (C=1.0, CHCl$_3$).

IR Spectrum (CHCl$_3$): 1775, 1715 cm$^{-1}$ (phthaloyl CO).

NMR Spectrum (CDCl$_3$): δ2.32 (3H, s,

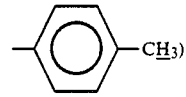

2.85-3.30 (2H, m,

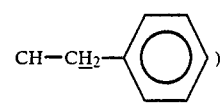

4.05-4.87 (3H, m, CH—CH$_2$—O), 7.06 (5H, s, phenyl group), 7.06 (2H, d, J=9.0 Hz, Ar.H), 7.58 (2H, d, J=9.0 Hz, Ar.H), 7.60 (4H, s, phthaloyl).

(5-3) Synthesis of (S)-(2-azido-1-benzyl)ethylphthalimide

Tetraethyl ammonium chloride (8.28 g; 0.05 mole) and 3.25 g (0.05 mole) of sodium azide were suspended in 200 ml of methylene chloride. The suspension was stirred at room temperature for 3 hours, and then filtered. The filtrate was dried under reduced pressure. To the residue were added 3.97 g (0.01 mole) of (S)-(1-benzyl-2-p-toluenesulfonyloxy)ethylphthalimide and 20 ml of anhydrous acetone. The mixture was refluxed for 18 hours. The reaction mixture was worked up in the same way as in (4-3) of Example 4, and adsorbed on a column of 200 ml of silica gel. The column was eluted with a benzene/ethyl acetate mixed solvent (20:1). Eluate fractions which had an ultraviolet absorption at an Rf value of 0.81 in silica gel thin-layer chromatography developed with a benzene/ethyl acetate mixed solvent (4:1) were collected and dried under reduced pressure to give 1.77 g of the captioned compound as a white powder.

$[\alpha]_D^{24}$: −86.7° (C=1.0, CHCl$_3$).

IR Spectrum (CHCl$_3$): 2200 cm$^{-1}$ (N$_3$) 1770, 1710 cm$^{-1}$ (phthaloyl CO).

NMR Spectrum (CDCl$_3$): 2.95-3.45 (2H, m,

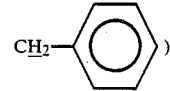

3.45-4.30 (2H, m, CH—CH$_2$—N$_3$), 4.63 (1H, m, CH), 7.13 (5H, s, phenyl group), 7.55-7.85 (4H, m, phthaloyl group).

(5-4) Synthesis of (S)-(2-amino-1-benzyl)ethylphthalimide 1.77 g (5.78 mmoles) of (S)-(2-azido-1-benzyl)ethylphthalimide was dissolved in a mixture of 50 ml of ethanol, 20 ml of dioxane and 18 ml of 1N HCl, and 500 mg of 10% Pd-C was added. It was catalytically reduced at room temperature and 4 atmospheres for 5 hours. The reaction product was dried under reduced pressure, and benzene was added. The insoluble material was collected by filtration to give 1.3 g of the hydrochloride of the captioned compound. This product showed color reaction with ninhydrin at an Rf value of 0.31 in silica gel thin-layer chromatography developed with methanol.

$[\alpha]_D^{24}$: −132.0° (C=1.0, MeOH)

IR Spectrum (KBr): 3200–2500 cm$^{-1}$ (NH$_3^+$) 1770, 1700 cm$^{-1}$ (phthaloyl CO)

NMR Spectrum (DMSO+D$_2$O): δ3.00–3.72 (4H, m,

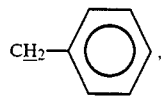

C$\underline{H}_2$—NH$_2$), 4.67 (1H, m, CH), 7.10 (5H, s, phenyl group), 7.75 (4H, s, phthaloyl group).

(5-5) Production of (S)-[N-(2-amino-2-benzyl)ethyl]glycine 1.5 g of (S)-(2-amino-1-benzyl)ethylphthalimide hydrochloride was dissolved in 100 ml of 50% methanol-water, and 1.5 g of sodium borohydride was added. They were reacted at room temperature for 3 hours. Acetic acid was added to the reaction solution to adjust its pH to 5.0. By silica gel thin-layer chromatography developed with methanol, a single spot showing color reaction with ninhydrin was determined at an Rf value of 0.21. Then, the pH of the reaction solution was adjusted to 10.5 with 2N sodium hydroxide, and it was extracted twice with 300 ml of ethyl acetate. The extract was dried under reduced pressure to give 1.26 g of (S)-(2-benzyl-2-o-hydroxymethylbenzylamino)ethylamine. This compound was dissolved in 100 ml of 50% dioxane-water, and 510 mg of sodium glyoxylate was added. They were reacted at room temperature for 1 hour. Furthermore, 1.1 g of sodium borohydride was added, and reacted at the same temperature for 18 hours. Acetic acid was added to the reaction solution to adjust its pH to 5.0, and its pH was further adjusted to 10.0 with 2N sodium hydroxide. The unreacted material was extracted with ethyl acetate. The aqueous layer was adjusted to pH 6.0, and dried under reduced pressure. 671 mg of the recovered material was dissolved in 24 ml of 50% dioxane-water, and similarly reacted with 296 mg of sodium glyoxylate. The reaction mixture was worked up in the same way. The residues were combined, and dissolved in 200 ml of concentrated hydrochloric acid. The solution was subjected to hydrolysis at 40° C. for 16 hours. The precipitate was removed by filtration and dried under reduced pressure. The residue was dissolved in water, adjusted to pH 3.5, and adsorbed on a column of 500 ml of Dowex 50W (H form). After washing with water, the column was eluted with 3N ammonium hydroxide. Eluate fractions which showed color reaction with ninhydrin at an Rm value of 1.10 in high-voltage paper electrophoresis at a pH of 1.8 were collected and dried under reduced pressure. The residue was further dissolved in water, and adsorbed on a column of 100 ml of Diaion PA306S (OH form). The column was washed with water, and then eluted with 1N HCl. Eluate fractions which showed color reaction with ninhydrin were collected and dried. The residue was dissolved in water, adjusted to pH 4.0 with Diaion PA306S (OH form), and precipitated with water-ethanol. The precipitate was collected by filtration to give 388 mg of the monohydrochloride of the captioned compound as a white powder.

Melting point: 157.5°–158° C.

$[\alpha]_D^{24}$: −9.3° (C=1.0, H$_2$O)

IR Spectrum (KBr): 3100–2300 cm$^{-1}$ (NH$_3^+$, NH$_2^+$) 1610 cm$^{-1}$ (COO$^-$).

NMR Spectrum (D$_2$O+DCl): δ2.93–3.36 (2H, m, CH$_2$), 3.51 (2H, d, J=6.5 Hz, CH$_2$), 3.68–4.26 (1H, m, CH), 3.80 (2H, s, HN—CH$_2$—COOH), 7.40 (5H, m, phenyl group).

Elemental analysis (for C$_{11}$H$_{17}$N$_2$O$_2$Cl): Found (%) C: 53.43, H: 6.88, N: 11.20. Calcd. (%) C: 53.99, H: 7.00, N: 11.45.

EXAMPLE 6

Production of (2-aminoethyl)thioacetic acid

Acetylcysteamine (1.5 g; 6.4 mmoles) was dissolved in a mixture of 50 ml of methanol and 10 ml of water, and 2 ml (15 mmoles) of tributylphosphine was added. They were reacted at room temperature for 18 hours. The reaction mixture was concentrated under reduced pressure, and then the reagent was removed by extraction. The aqueous layer was concentrated under reduced pressure and used in the subsequent reaction. Specifically, the residual acetyl cysteamine (1.5 g) was mixed with 1.78 g (12.8 mmoles) of bromoacetic acid and 25.6 ml of 1N sodium hydroxide and reacted at 80° C. for 2 hours. The reactive solution was adsorbed on a column of 70 ml of Dowex 1 (OH form). The column was washed with water, and eluted with 1N HCl. The eluate was dried under reduced pressure. The residue was dissolved in 200 ml of 2N HCl, and hydrolyzed at 100° C. for 5 hours. The product was dried under reduced pressure, and adsorbed on a column of 80 ml of Dowex 50W (H form) at a pH of 6.0. The column was washed with water, and then eluted with 3N ammonium hydroxide. The eluate was dried under reduced pressure, and recrystallized from water-ethanol to give 533 mg of the captioned compound as colorless needles. This compound showed an Rm value of 1.4 in high-voltage paper electrophoresis at a pH of 1.8.

Melting point: 168.5°–169.5° C.

IR(KBr): 3150–2500 cm$^{-1}$ (NH$_3^+$), 1570 cm$^{-1}$ (COO$^-$).

NMR(D$_2$O): δ2.92 (2H, t, J=6.5 Hz, CH$_2$), 3.27 (2H, t, J=6.5 Hz, CH$_2$), 3.30 (2H, s, S—CH$_2$—COO).

Representative formulations containing compounds of the present invention and carbapenem antibiotics can be prepared by the following procedures:

EXAMPLE A

Capsules

| Component | Per capsule |
|---|---|
| Antibiotic PS-5 (sodium salt) | 100 mg |
| Compound (No. 5) | 200 mg |
| Lactose (J. P.) | a sufficient amount |
| Magnesium stearate | 1 mg |

The active compounds and the diluents are well mixed to produce a uniform blend. Two hundred milligrams of the blend is filled in a No. 3 hard gelatin capsule.

EXAMPLE B

Tablets

| Component | Per tablet |
|---|---|
| Antibiotic PS-5 (sodium salt) | 200 mg |
| Compound (No. 1) | 500 mg |
| Lactose (J. P.) | 120 mg |
| Corn starch | 175 mg |
| Magnesium stearate | 5 mg |

In the above composition, the active component is blended with lactose and a half amount of corn starch.

The mixture is granulated with 10% of the above amount of corn starch paste and screened. The balance of corn starch and magnesium stearate are added and the mixture is compressed into tablets, approxmately 1 cm in diameter, each weighing 500 mg.

EXAMPLE C

Lyo form for injection

| Component | Per vial |
|---|---|
| Antibiotic PS-5 (sodium salt) | 25 mg |
| Compound (No. 5) | 25 mg |

The active component is dissolved in sterile dissolved water for injection, filtered and sterilized. The solution is subdivided into sterile vials, and water is aseptically removed by lyophilization. The vials containing the sterile dry solid are aseptically sealed.

To restore for parenteral administration, 2 ml of sterile physiological saline is added to the content of a vial.

EXAMPLE D

Tablets

| Component | Per tablet |
|---|---|
| Antibiotic PS-5 (sodium salt) | 25 mg |
| Cephaloridine | 180 mg |
| Compound (No. 1) | 500 mg |
| Lactose (J. P.) | 120 mg |
| Corn Starch | 175 mg |
| Magnesium stearate | 5 mg |
| | 1000 mg |

Antibiotic PS-5 and cephaloridine are mixed with the other ingredients and compressed into tablets as described in Example B. The tablets are covered first with a sugar coating and then with an enteric coating.

What is claimed is:

1. A compound represented by the formula

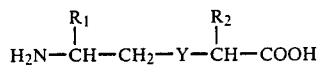

wherein $R_1$ and $R_2$ independently of each other represent a hydrogen atom or alkyl of up to 10 carbon atoms which is unsubstituted or substituted by 1 to 3 substituents selected from the group consisting of cycloalkyl of up to 6 carbon atoms, phenyl, naphthyl, hydroxyphenyl, hydroxy, mercapto, lower alkyl mercapto, carboxy, amino, carbamoyl, guanidyl, pyrrolidinyl, imidazolyl and indolyl, and Y represents —NH— or —S—, with the proviso that when Y represents —NH—, at least one of $R_1$ and $R_2$ represents an alkyl group which may be substituted, and with the further proviso that when Y represents —S—, at least one of $R_1$ and $R_2$ represents an alkyl group which may be substituted.

2. A dipeptidase inhibitor composition comprising a compound of the formula

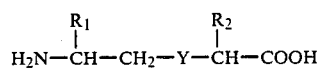

wherein $R_1$ and $R_2$ independently of each other represent a hydrogen atom or alkyl of up to 10 carbon atoms which is unsubstituted or substituted by 1 to 3 substituents selected from the group consisting of cycloalkyl of up to 6 carbon atoms, phenyl, naphthyl, hydroxyphenyl, hydroxy, mercapto, lower alkyl mercapto, carboxy, amino, carbamoyl, guanidyl, pyrrolidinyl, imidazolyl and indolyl, and Y represents —NH— or —S—, and a pharmaceutically acceptable inert carrier or diluent.

3. A compound of claim 1 wherein Y represents —NH—.

4. A compound of claim 1 wherein $R_1$ represents a lower alkyl group and $R_2$ represents a hydrogen atom.

5. A compound of claim 1 wherein $R_1$ represents a benzyl group and $R_2$ represents a hydrogen atom.

6. A dipeptidase inhibitor of claim 2 wherein Y represents —NH.

7. A dipeptidase inhibitor of claim 2 wherein $R_1$ and $R_2$ are both hydrogen atoms.

8. A dipeptidase inhibitor of claim 2 wherein $R_1$ represents a lower alkyl group and $R_2$ represents a hydrogen atom.

9. A dipeptidase inhibitor of claim 2 wherein $R_1$ represents a benzyl group and $R_2$ represents a hydrogen atom.

10. A compound according to claim 1 wherein $R_1$ is benzyl, $R_2$ is hydrogen and Y is —NH—.

* * * * *